US005763656A

United States Patent [19]

Klasen et al.

[11] Patent Number: 5,763,656
[45] Date of Patent: Jun. 9, 1998

[54] METHOD OF PREPARING TARTARIC ACID

[75] Inventors: Ralf Klasen, Leverkusen; Hermann Sahm, Jülich; Ingo Matzerath, Leverkusen, all of Germany; Wolfgang Kläui, Vaals, Netherlands

[73] Assignee: Forschungszentrum Julich GmbH, Julich, Germany

[21] Appl. No.: 849,006

[22] PCT Filed: Nov. 8, 1995

[86] PCT No.: PCT/DE95/01568

§ 371 Date: May 8, 1997

§ 102(e) Date: May 8, 1997

[87] PCT Pub. No.: WO96/15095

PCT Pub. Date: May 23, 1996

[30] Foreign Application Priority Data

Nov. 10, 1994 [DE] Germany ............ 44 40 191.4

[51] Int. Cl.⁶ .......... C07C 51/16; C07C 51/245; C07C 59/255

[52] U.S. Cl. .......... 562/527; 562/585

[58] Field of Search .......... 562/527, 585

[56] References Cited

U.S. PATENT DOCUMENTS

| 1,425,605 | 8/1922 | Odell | 562/515 |
| 2,197,021 | 4/1940 | Pasternack et al. | 260/536 |
| 2,380,196 | 7/1945 | Soltzberg | 562/531 |
| 2,419,019 | 10/1947 | Hales | 562/531 |
| 2,419,038 | 4/1947 | Sanders | 562/531 |
| 3,585,109 | 6/1971 | Yamada et al. | 435/145 |
| 4,092,220 | 5/1978 | Tsurumi et al. | 435/145 |

*Primary Examiner*—Gary Geist
*Assistant Examiner*—Rosalynd Keys
*Attorney, Agent, or Firm*—Herbert Dubno

[57] ABSTRACT

A method of preparing tartaric acid in which 5-ketogluconate is oxidized in a carbonate buffer at an alkaline pH preferably in the range of 8 to 10 using vanadate.

3 Claims, 1 Drawing Sheet

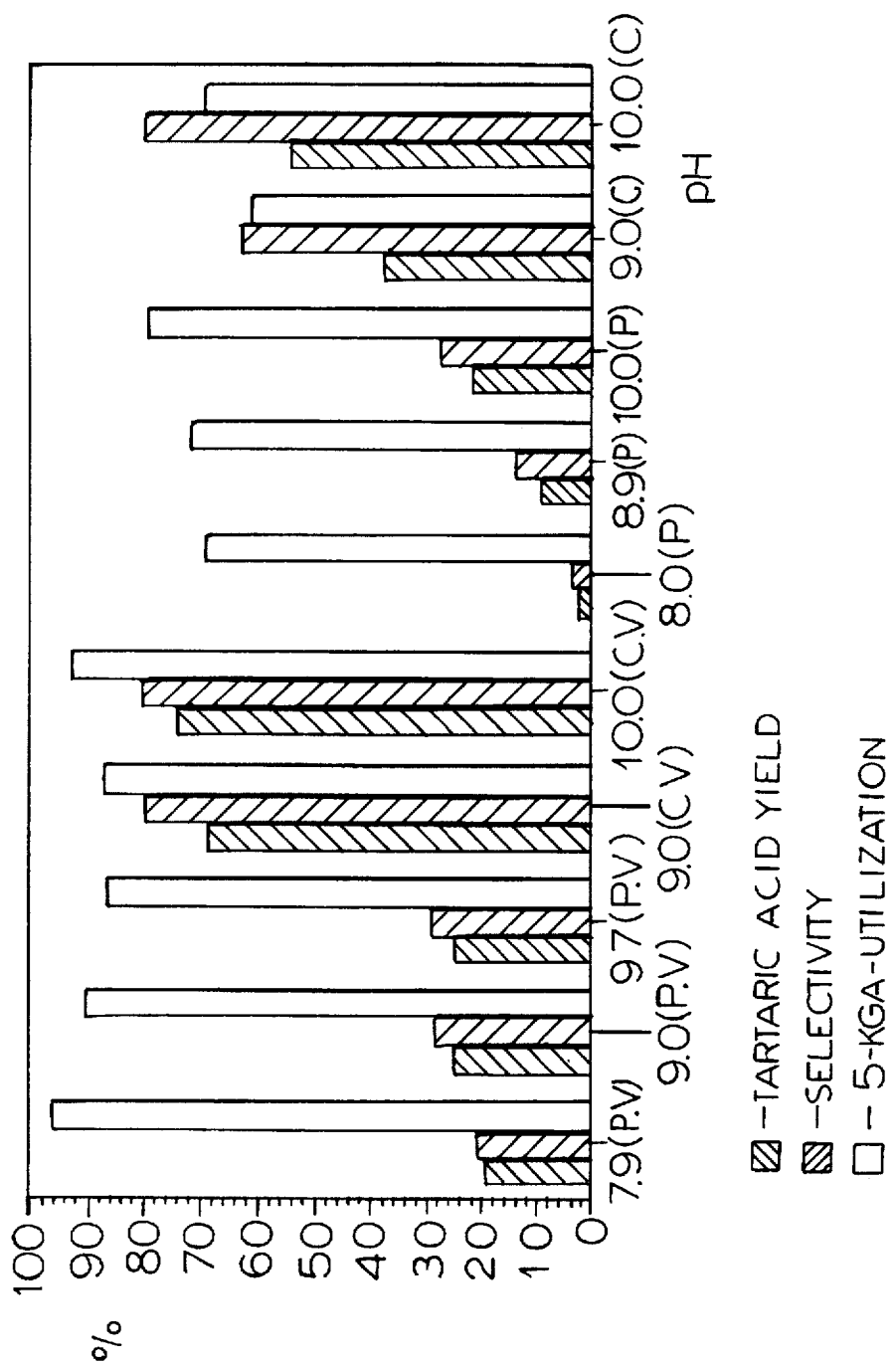

METHOD OF PREPARING TARTARIC ACID

This application is a 371 of PCT/DE95/01568, filed Nov. 8, 1995.

The invention relates to a method of producing tartaric acid.

Tartaric acid is used above all in many applications in the food and textile industries. For example, tartaric acid is used as a food additive, especially as an antioxidant and acidification agent. In addition, tartaric acid is used as a building material additive for modification of the setting characteristics of cement and serves as a starting substance for numerous chemical reactions, especially for chiral synthesis. One way of producing tartaric acid is to recover it from tartar, a substance which is produced during the production of wine. However, the crude tartar which results from the production of wine is as a rule contaminated by organic materials so that expensive preparation is necessary to obtain the tartaric acid from the tartar.

Because of this drawback, alternatives for the production of tartaric acid have been developed. For example, in U.S. Pat. No. 1,425,605 the production of tartaric acid by oxidation of carbohydrates in the presence of nitrate is described. This procedural method gives rise to various stereoisomers of the tartaric acid and is thus relatively unselective. The yield of the tartaric acid achieved chemically based upon the starting substances used is relatively low. For example, the yield, upon the conversion of 5-ketogluconate or other carbohydrates to tartaric acid using nitric acid as the oxidation agent is about 10% (U.S. Pat. No. 2,380,196) to a maximum of about 40% (W. E. Barch, J. Am. Chem. Soc. 55, 3653, 1933). The conversion of 5-ketogluconic acid to tartaric acid in an alkaline milieu with 1M calcium hydroxide solution or sodium hydroxide gives rise to tartaric acid yields up to about 10% (H. Isbell and N. Hold, The Journal of Research of the Bureau of Standards 35, 433, 1945).

A further process for producing tartaric acid resides in the conversion of glucose to tartaric acid through microorganisms like acetobacter or gluconobacter in the presence of vanadate as trace element (compare U.S. Pat. No. 3,585,109). It can be demonstrated that in these processes the tartaric acid production is carried out in two steps. In the first step 5-ketogluconate is excreted into the medium of microorganisms cultured in a glucose-containing medium, while in a second step the conversion of 5-ketogluconate to tartaric acid is carried out purely chemically with the vanadium salt as trace element, i.e. independently of the presence of microorganisms (R. Klasen, S. Bringer-Meyer and H. Sahm, Biotechnology and Bioengineering 40, 183, 1992). This production process has especially the advantage that only one isomer of the tartaric acid, namely, the desired L-(+)-tartaric acid arises. However, the conversions hitherto achieved with this conversion of 5-ketogluconate to tartaric acid remains unsatisfactory.

It is the object of the invention to provide a simple process for the production of tartaric acid in which a higher conversion of 5-ketogluconate to tartaric acid can be obtained.

This object is achieved, in accordance with the invention, in that 5-ketogluconate is converted to tartaric acid in a carbonate buffer oxidatively at an alkaline pH.

It has been found surprisingly that under these reaction conditions, i.e. also without the addition of vanadate or another catalyst, a conversion of 5-ketogluconate to tartaric acid results whereby a conversion of 5-ketogluconic acid to tartaric acid of up to 55% is achieved.

If vanadate is additionally supplied to the reaction mixture, conversions up to 75% of the 5-ketogluconate used to tartaric acid are obtained. In the presence of another buffer, like for example an alkali borate buffer, the tartaric acid formation by contrast is completely blocked.

The pH range in which the conversion is preferably carried out encompasses the range from pH 8 to pH 10.

EXAMPLE 2.0 ml of an 0.50M solution of the potassium salt of 5-ketogluconic acid is prepared in a 20 ml measuring flask. 0.40 ml of a 50 mM ammonium vanadate solution is added and the flask is filled with 0.50M carbonate or phosphate buffer (ph 10.0) to 20 ml. Analogously solutions with 0.40 ml water in stead of ammonium vanadate are produced After mixing of the components, the pH value of the solution was determined and the reaction mixture is filtered into previously autoclaved 50 ml Erlenmeyer flasks. The flasks are sterilely closed with Watte stoppers and are shaken in an incubation shaker at 27° C. and 180 RPM for eight days.

The solution of 5-ketogluconic acid and the amount of tartaric acid formed are then determined by means of HPLC. From these values the yield and selectivity of the reaction is determined. The results are shown in FIG. 1.

In FIG. 1:

C: Carbonate buffer, P: phosphate buffer, V: vanadate, TA: tartaric acid, 5-KGA: 5-ketogluconate.

Yield: conversion of the 5-ketogluconate used to tartaric acid whereby the conversion of 1 mole of 5-ketogluconic acid to 1 mole of tartaric acid is set equal to 100%.

Selectivity: conversion of the 5-ketogluconate to tartaric acid.

As is apparent from FIG. 1, tartaric acid yield upon conversion of 5-ketogluconic acid in phosphate buffer with vanadate as a catalyst and an alkaline pH value is about 25% while in carbonate buffer it is about 75%. There is also a conversion of 5ketogluconate to tartaric acid without the catalyst whereby the tartaric acid yield in carbonate buffer at pH 10 reaches about 55%. Furthermore, the selectivity on conversion of 5-ketogluconate in carbonate buffer with values between 65 to 75% is relatively high— which is consistent with a reduced byproduct formation. Thus under the selected reaction conditions the greatest portion of the 5-ketogluconic acid is converted to tartaric acid.

We claim:

1. A method of producing tartaric acid in which 5-ketogluconate is converted oxidatively to tartaric acid in a carbonate buffer at an alkaline pH value.

2. The method according to claim 1 characterized in that the conversion is carried out with vanadate.

3. Process according to claim 1 characterized in that the conversion is preferably carried out in a pH range of 8 to 10.

* * * * *